Figure 1:
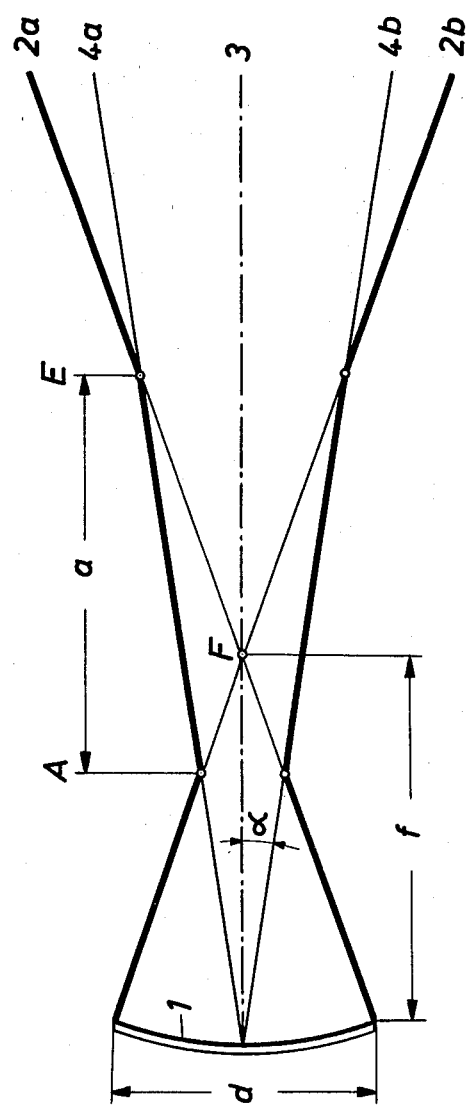

United States Patent [19]

Kretz

[11] 4,403,509

[45] Sep. 13, 1983

[54] ULTRASONIC EQUIPMENT FOR EXAMINATIONS USING SECTION IMAGES

[75] Inventor: Carl Kretz, Zipf, Austria

[73] Assignee: Kretztechnik Gesellschaft mbH, Zipf, Austria

[21] Appl. No.: 275,874

[22] Filed: Jun. 22, 1981

[30] Foreign Application Priority Data

Jul. 15, 1980 [AT] Austria .................................. 3663/80

[51] Int. Cl.$^3$ ............................................ G01N 29/04
[52] U.S. Cl. ......................................... 73/639; 73/626
[58] Field of Search ................................... 73/639, 626

[56] References Cited

U.S. PATENT DOCUMENTS

| | | | |
|---|---|---|---|
| 3,693,415 | 9/1972 | Whittington | 73/626 |
| 4,102,204 | 7/1978 | Kretz | 73/626 |
| 4,229,978 | 10/1980 | Sholl et al. | 73/626 |

*Primary Examiner*—Anthony V. Ciarlante
*Attorney, Agent, or Firm*—Kurt Kelman

[57] ABSTRACT

Ultrasonic equipment for examinations using section images comprises a scanning mechanism, which includes a wheel that can be driven to rotate and carries a plurality of focussing sound transducer heads having working ranges which cover only respective fractional parts of the depth of the section surface. Each sound transducer head is activated as the sound beam emitted by the sound transducer head moves in the section surface. The echoes received by the sound transducer heads are used to generate a section image. In order to improve the image quality, sound transducer heads having working ranges in different depths of the section surface are activated in succession. Pre-entry paths are associated with sound transducer heads for examining regions near the surface of the object to be examined. Selecting means are provided which ensure that only echo signals derived from echoes which have originated in the working range of an activated sound transducer head are used to generate the image.

8 Claims, 5 Drawing Figures

*FIG. 4*
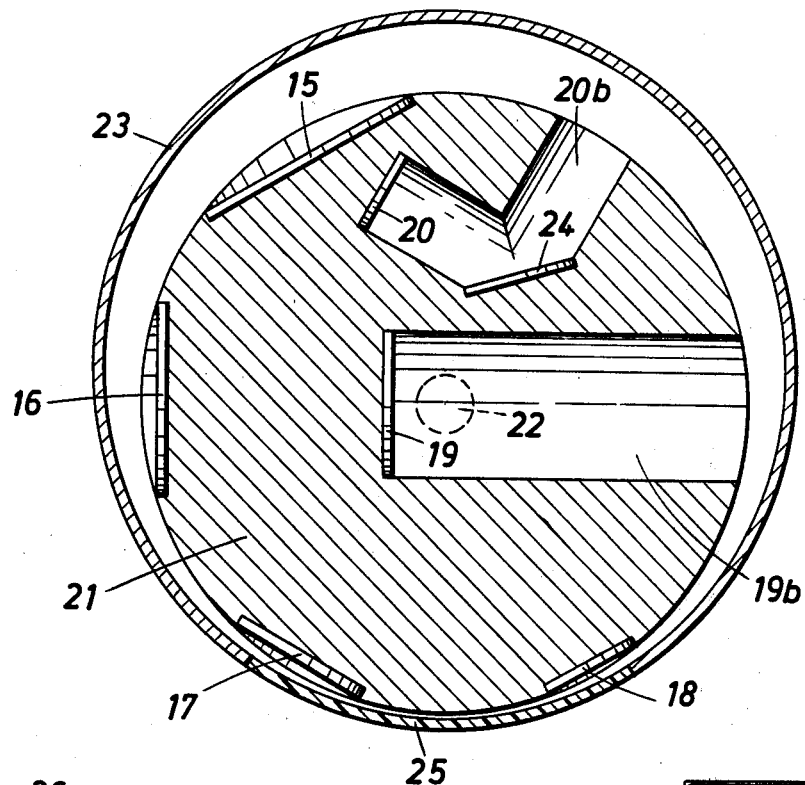
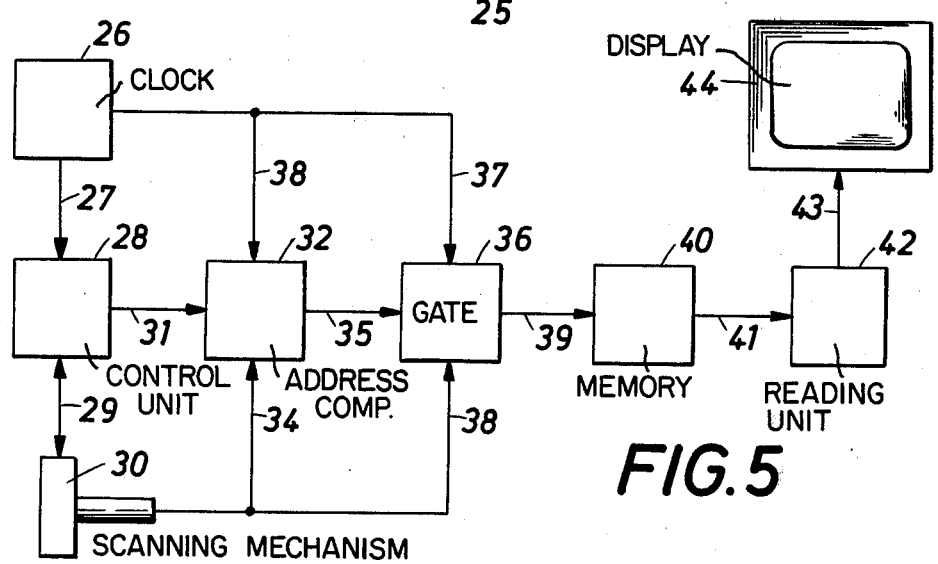
*FIG. 5*

ULTRASONIC EQUIPMENT FOR EXAMINATIONS USING SECTION IMAGES

This invention relates to ultrasonic equipment for examinations using section images, comprising a scanning mechanism including a wheel, which is adapted to be driven to rotate, a plurality of focussing sound transducer heads, which are carried by the wheel and angularly spaced apart, each of which sound transducer heads is adapted to be activated to emit sound pulses in the form of a sound beam into a section surface of an object to be examined, to receive echoes originating in said section surface in response to said sound pulses and to derive echo signals from said echo pulses, said sound transducer heads being adapted to scan said section surface with an improved resolution in respective working ranges, which extend in different fractional parts of the section surface, means for activating each of said sound transducer heads when said wheel is in an angular position in which the sound transducer head is adapted to direct a sound beam into said section surface, and a display unit for displaying said echo signals on a display surface at locations which are geometrically coordinated with the locations at which the corresponding echoes have originated in the section surface.

Ultrasonic equipment of that kind has been disclosed in U.S. Pat. No. 4,102,204 of the same inventor. In the known equipment disclosed, the wheel is accommodated in a housing, which is filled with a sound-conducting liquid and has a diaphragm, which constitutes a sound exit window, and the sound transducer heads are mounted on the wheel at the periphery thereof and are adapted to be activated as they move past the window so that the sound travels in the housing in a short pre-entry path before it is emitted from the outside of the window. The length of that pre-entry path is of an order of a wavelength of sound, i.e., negligibly small, so that the sound is virtually directly introduced into the object to be examined. The sound transducer heads are activated by means of change-over switches or by means of a transformer, which comprises a winding that rotates in unison with the wheel and a second winding, which is stationary. Such ultrasonic equipment is simple in design and can move the sound beam at a uniform angular velocity so that a uniform lateral resolution will be obtained if the pulse repetition frequency is constant, without a need for additional measures. The section surface which is scanned has the configuration of a sector of a circular ring, approximately a trapezoid, so that there will be no need for relocating the mechanism if a sufficiently wide strip near the surface of the object is to be examined, provided that the wheel is sufficiently large in diameter. A basic advantage of the virtually direct introduction of the sound beam resides in the fact that virtually only the transit times of the sound pulses and of the echoes in the object must be taken into account in the determination of the pulse repetition frequency.

The sound transducer heads of other known equipment are also driven to rotate but are activated when they face a parabolic reflector so that the sound beams are reflected before entering the object to be examined. In that equipment the sound beams must travel in a pre-entry path for a transit time which exceeds the transit time of the sound pulses and echo pulses in the object, in order to avoid so-called ghost echoes. Whereas such equipment can be used to scan an approximately rectangular section surface, it cannot be used for a scanning to a large depth unless the pulse repetition frequency is very low so that it will be difficult to prevent flickering in moving section images as the highest permissible pulse repetition frequency is reduced to one-half of that frequency in equipment of the kind described first hereinbefore. During an operation at a constant pulse repetition frequency and constant angular speed, the reflection at the parabolic reflector will result in a non-uniform lateral resolution.

It is also known to use focusing sound transducer heads. Besides, it is known to provide a plurality of groups of focusing sound transducer heads having equal focal lengths and to use all sound transducer heads of a group to produce one section image or to provide each sound transducer head with two generators, specifically a circular generator and one having the shape of a circular ring, and to vary the zone of maximum sensitivity by a change of the emitting surface, i.e., that one generator or the other is selectively activated or both generators are activated at the same time. In any case, focusing results in a sound beam which in a certain range is constricted, i.e., smaller in diameter, than the sound beam transmitted by a non-focusing sound transducer head, and the lateral resolution is thus improved. On principle, focusing can be effected by a lens, by the use of a curved generator, or in that annular generator zones are excited at different phases. The sound beam is constricted only in a certain depth range, i.e., at a certain distance from the generator, and only in a certain length. Outside that range the sound beam is more divergent than a normal sound beam. In the present application and claims, that range in which the lateral resolution is actually higher than can be obtained by a non-focussing sound transducer head under given conditions, will be described as the "working range" of the sound transducer head. An exact definition of that working range will be given in the detailed description of the drawings. The working range will be the shorter, the smaller the focal length of the focussing sound transducer head so that the distance from the sound transducer head to the working range will be small if the focal length is small; larger focal lengths will result in a longer working range but the near end of the working range will be spaced a larger distance from the sound transducer head. In known ultrasonic equipment having focussing sound transducer heads it is virtually impossible to obtain during a single scan of the section surface of working range which extends throughout the depth of the scanning surface. If it is attempted to examine regions near the surface of an object with a focused sound beam which has been virtually directly introduced, the sound transducer heads having correspondingly short focal lengths will have only extremely short working ranges. Besides, if the sound beam is introduced directly, there will be interferences between the emitted sound pulses and echoes from regions near the object of the surface.

Equipment for an indirect introduction of the sound beam over a distinct pre-entry path is more suitable for an examination of regions near the surface of the object but, as has been stated hereinbefore, the frame frequency can be only very low in such cases and must be selected in consideration of the length of the pre-entry path and the largest possible depth of penetration of the sound beam into the object.

It is an object of the invention to provide ultrasonic equipment which is of the kind described first hereinbefore and by which the improvement of the image quality that results from the focusing can be extended over a major portion of the depth or the entire depth of the section surface and regions near the surface of the object can be examined too. Another object of the invention is to permit an examination at a sufficiently high pulse repetition frequency.

This object is accomplished in that the sound transducer heads, which are adapted to scan the section surface with improved resolution in working ranges extending in different fractional parts of the depth of the section surface, are adapted to be activated in succession, means defining pre-entry paths are associated with at least one sound transducer head which serves to examine the section surface near the surface of the object, and selecting means are provided for selecting the echo signals derived from echoes that have originated in the working range of an activated sound transducer and for delivering only the selected echo signals to signal-processing means for a display by said display unit.

In this way, only the echoes which have originated in the working ranges of the sound heads activated in succession will be utilized to generate the image and the entire image will have a higher resolution. The sound beams for examining the section surface in a relatively large depth can be introduced virtually directly into the object and the zone or zones which is or are near the surface of the object may be examined with sound beams which have traveled in a pre-entry path. If the depths of penetration of the beams which have traveled in a pre-entry path are restricted, only such restricted depth of penetration will have to be taken into account in the selection of the pulse repetition frequency and the length of the pre-entry path so that the same pulse repetition frequency can be used as for the examination of zones in larger depths by directly introduced sound beams. Alternatively, sound at different frequencies may be used for an examination at different depths. Particularly, regions near the surface may be examined with sound at higher frequencies than regions at larger depths. Higher sound frequencies will inherently involve a higher resolution and will also involve a lower depth of penetration into the object, which may consist of organic tissue. That lower depth of penetration may be desirable in such case as it will help to avoid ghost echoes.

In practice, the sound transducer heads will be adjusted so that their working ranges will adjoin and will cover the depth of the section surface without gaps.

A particularly pleasing and uniform image will be obtained if the sound transducer heads are adapted to emit sound beams which have the same mean diameter and the same maximum diameter in the several working ranges. It will be understood that the known measures for improving the display will preferably be used, such as a so-called depth compensation (amplification of echo signals in dependence on transit time), and that circuits for suppressing disturbing secondary echoes will be provided, if desired.

In a simple embodiment, the selecting means may comprise an electronic gate, which is open during times which are controlled by the scanning mechanism in dependence on the working range of the sound transducer head which is just activated. In the simplest case the sound transducer heads for scanning adjacent depth zones are juxtaposed, i.e., arranged in succession, on the wheel. Such an arrangement will permit a particularly simple control of the gate which has just been mentioned because the time at which the gate is to be closed during the scanning movement of one sound transducer head will correspond to the time at which the gate is to be opened during the scanning movement of the next following sound transducer head. For reasons of space economy or in order to obtain a more uniform illumination of the display surface, sound transducer heads having working ranges which correspond to spaced apart depth zones of the section surface may be arranged in succession on the wheel. Finally, the sound transducer heads carried by the wheel may be regarded as a group of sound transducer heads, at least one additional group of identical sound transducer heads may be provided and each of the sound transducer heads of such addition group may be used to scan the section surface throughout its depth. If the wheel is rotated at constant speed and each group consists of the same number of sound transducer heads, the sound transducer heads of the group designed in accordance with the invention may be used to produce section images having a high lateral resolution and the sound transducer heads of the additional group or groups may be used to obtain a higher time resolution, i.e., a frame frequency which is sufficiently high for a satisfactory display of fast motions.

In order to obtain a satisfactory image quality so that it will be possible in case of need to display the section image on a conventional television monitor and also to permit the generation of still pictures of motions, in case of need, for an observation for a relatively long time, another embodiment comprises in a manner known per se a buffer memory for the echo signals to be interpreted and a reading unit for delivering the signals to the display unit. The echo signals are stored in the memory at addresses coordinated with the locations at which the corresponding echoes have originated in the section surface. The memory may constitute an overwrite memory or may be provided with a program-controlled unit, which compares signals just received with signals stored at the associated address and in accordance with the program generates new signals, which are stored at the associated address. The memory contains at any time all echo signals for a complete section image so that when the memory is read the entire section image is displayed in a uniform image quality. When the reception of signals is interrupted, the last total image which has been stored can be observed further as a still image.

In another embodiment of the invention, at least those sound transducer heads which are intended to scan the section surface near the surface of the object are accommodated inside the wheel and pre-entry paths are provided between the sound-emitting surface of said sound transducer heads and a sound exit provided at the periphery of the wheel. Said pre-entry paths may be constituted in known manner by synthetic resin elements having suitable sound-conducting properties. The design can be further simplified in that the pre-entry paths are constituted by sound-conducting liquid in bores or passages formed in the wheel body. If the diameter of the wheel or the space available inside the wheel is so small that it is impossible or difficult to provide straight pre-entry paths of sufficient lengths, at least one pre-entry path may be angled once or several times in that the sound is reflected by suitable reflectors.

A preferred design will be obtained if the wheel, as is known from the above-mentioned publications, is accommodated in a housing, which is filled with a sound-conducting liquid and has a sound exit window formed by a diaphragm, and each of those sound transducer heads which are mounted at the periphery of the wheel is activated as it moves past the window so that the sound emitted by such sound transducer head will exit from the outside of the window after having passed only through a small pre-entry distance, which is of an order not in excess of the wavelength of the sound. In accordance with the invention the liquid which constitutes the pre-entry paths for the sound beams for examining the section surface near the surface of the object is accommodated in bores or passages which are open to the interior of the housing at the periphery of the wheel. Under control by change-over switches, the sound transducer heads with which pre-entry paths are associated may be operated at a lower pulse repetition frequency than the other sound transducer heads, and said change-over switches may be mechanically or optically or electronically controlled in dependence on the rotation of the wheel.

Figure 2:
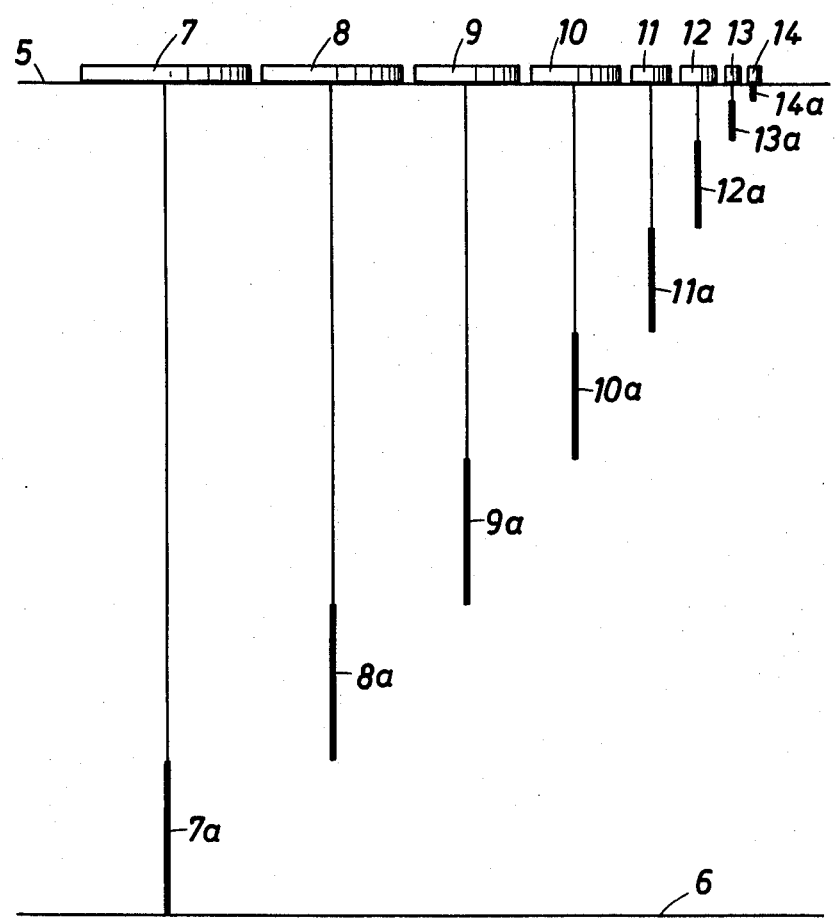
Figure 3:
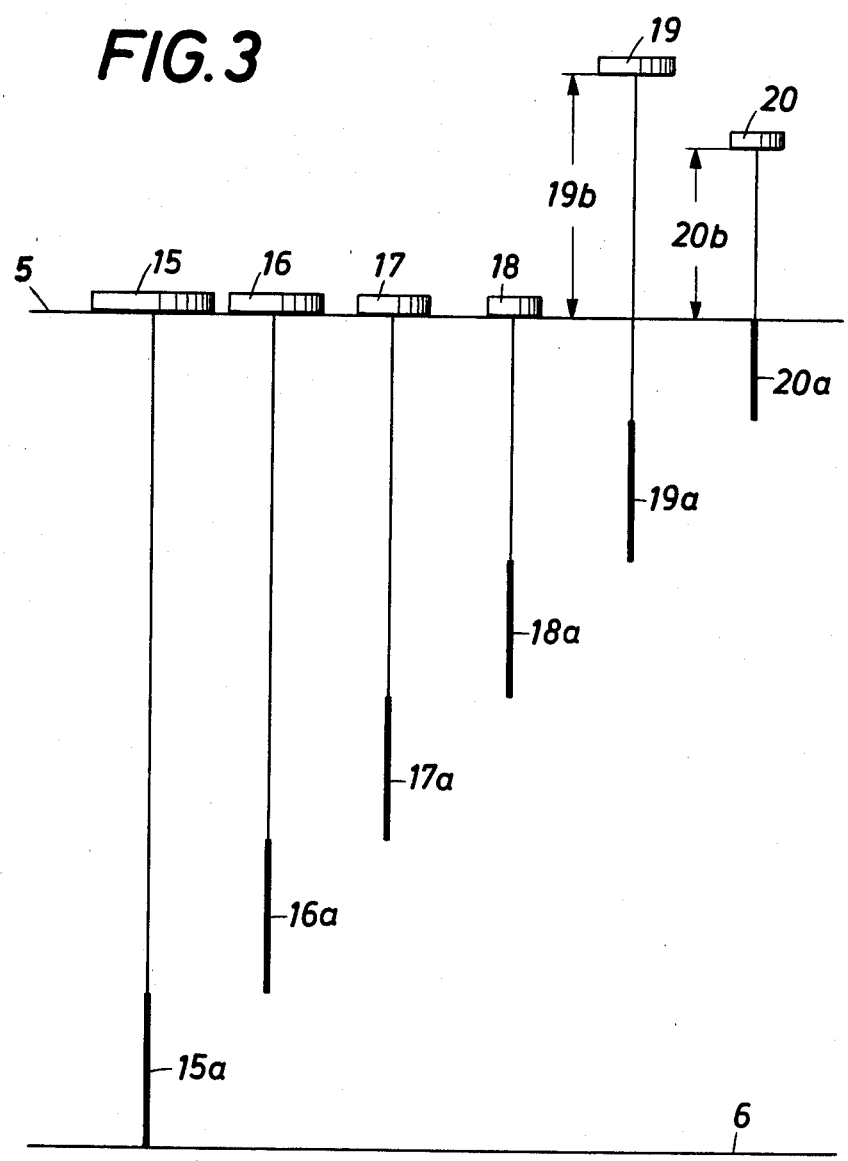

An embodiment of the invention will now be described by way of example with reference to the accompanying drawings, in which FIG. 1 shows a simple approximation construction which serves to explain the physical relationships and permits a determination of the sound field of a focusing sound transducer head with adequate accuracy, FIG. 2 is a diagrammatic representation showing juxtaposed working ranges of different sound transducer heads, FIG. 3 is a similar diagram, which relates to a group of sound transducer heads some of which have pre-entry paths associated with them, FIG. 4 is a sectional view, which is taken on a plane that is transverse to the axis of rotation of the wheel and shows the scanning mechanism of equipment embodying the invention, and FIG. 5 is a block circuit diagram of equipment according to the invention.

In accordance with an approximation construction developed by the assignees of the inventor the operation of a focussing sound transducer head 1 results in the conditions shown in FIG. 1. In spite of the simplicity of the construction, the actual conditions cannot be illustrated with adequate accuracy.

The focussing sound transducer head 1 has been shown as a concave-faced generator having a diameter d. A planar generator in combination with a sound lens arranged in front of the generator could also be used or a planar generator which is divided by annular electrodes into a plurality of annular zones, which are excited at different phases so that focussing will be effected. The focal length f of the generator 1 depends on the curvature of the generator and is equal to the radius of curvature. Where acoustic lenses are used or annular zones, which are excited at different phases the focal length will also have a value which can be exactly determined. An approximation of the sound field generated by the focussing sound transducer head will be obtained if straight lines $2a$, $2b$ are drawn from the rim of the generator 1 through the focal point f and additional straight lines $4a$, $4b$ from the center of the face of the generator are drawn on both sides of the axis 3 at an angle of taper $\alpha$ thereto, which is equal to the angle of taper of a non-focusing sound transducer head having the diameter d and operated at the wavelength $\lambda$. That angle $\alpha$ is calculated by the equation $$\sin \alpha = 1.22(\lambda/d) \tag{1}$$

The envelope of the sound beam is represented by a thick line in FIG. 1. The strongly constricted region of the sound beam in which the properties of the sound beam are markedly improved is called the working range a of the sound transducer head. That working range extends from A to E and has the length shown on the drawing. This does not mean that the sound transducer head can be used for examination only in the working range a. The working range a is merely the range in which the sound transducer head 1 has markedly improved properties in comparison with a non-focussing sound transducer head which is of the same size and operated at the same frequency. The following approximation equations derived from the construction shown in FIG. 1 and equation (1) can be used to calculate the distances $l_A$ and $l_E$ from the center of the face of the sound transducer head to the near and far ends of the working range:

$$l_A = fd^2/(d^2 + 2.44\lambda f) \tag{2}$$

and $$l_E = fd^2/(d^2 - 2.44\lambda f) \tag{3}$$

Depending on the diameter d, the focal length f and the wavelength $\lambda$, these two lengths determine the near and far ends of the working range and its length but also the diameter of the sound beam; that diameter determines the lateral resolution. These parameters are mathematically related to each other so that when three of these parameters have been selected all remaining parameters will be clearly defined. Additional restrictions occur in practice. As the wavelength decreases, the sound is increasingly attenuated in an object to be examined. For this reason the wavelength must exceed a certain minimum if a given depth of penetration is required. For a high resolution in depth, the wavelength should be as close as possible to that minimum.

A definite case has been calculated for by way of example. It has been assumed that a depth of penetration of 200 mm is required. A wavelength has been selected which by experience ensures that depth of penetration. It was also required that the diameter of the sound beam at the far end of the working range should not exceed a predetermined value. The diameter of the generator and the focal length were calculated as well as the location of the near end of the working range. The calculation showed that the working range a has a length of only 38 mm and its near end is spaced 162 mm from the center of the face of the generator. At a depth of penetration of 200 mm, only said end zone having a length of 38 mm can be examined with an improved lateral resolution.

In accordance with the invention, sound transducer heads are used which have working ranges corresponding to adjoining depth zones, which together extend through the desired depth range. When the section image to be generated is required to represent the section surface from the surface of the object to a depth of 200 mm, the result shown in FIG. 2 will be obtained, where line 5 represents the surface of the test specimen or the object to be examined and line 6 represents the largest depth of penetration desired. To permit an examination of the object throughout the desired depth with an improved resolution, the focussing sound transducer heads 7 to 14 have been provided, each of which has been represented only by its generator. The corresponding working ranges have been designated 7a, 8a etc. It is seen that smaller generators having shorter working ranges 7a, 8a are used to obtain zones of improved resolution which are nearer to the surface 5. This fact gives rise to various difficulties in practice. In the first place, a relatively large number of sound transducer heads are required in order to obtain working ranges which cover the entire depth range which is desired. Eight sound transducer heads 7 to 14 are required in the example which has been selected. If these eight sound transducer heads are mounted on a wheel with a regular angular spacing, said angular spacing will amount to 45°. In practice the angular movement which can be utilized to generate a section image is smaller than said angular spacing. If a larger usable angular movement is desired, some of the sound transducer heads, e.g., the sound transducer heads 12, 13 and 14, may be omitted so that regions near the surface of the object are not examined at all or are examined with a non-optimum resolution in that the generator 11 is used for an examination also on the left of point A. The manufacture of sound transducer heads which are required for an examination of regions near the surface to the object and which emit sound directly into the object to be examined involves high technological difficulties because such sound transducer heads are small in diameter and must have short focal lengths. In case of a direct introduction of sound, part of the theoretical length of the working ranges cannot be utilized near the surface of the object because echoes generated here will be disturbed by the emitted sound pulses. For this reason it is recommendable to associate pre-entry paths with sound transducer heads used to examine regions near the surface of the object. It has been shown hereinbefore that the usable length of a working range increases with its distance from the sound transducer head. The provision of pre-entry paths permits the use of focussing sound transducer heads having longer working ranges so that a smaller number of sound transducer heads will be sufficient to cover the section surface in the desired depth range with working ranges of improved resolution. Besides, the zone in which the echoes are disturbed by the emitted sound pulses will lie in the pre-entry path, outside the object being examined. The length of the pre-entry path should be at least as large as the maximum depth of the zone to be examined by said sound transducer head. For this reason it is recommended to associate pre-entry paths only with those sound transducer heads which serve to examine regions near the surface of the object whereas the remaining sound transducer heads are coupled to the object to be examined as closely as possible when the sound transducer heads are activated because otherwise long pre-entry paths would have to be associated with the sound transducer heads for examining zones in larger depths and this would lower the highest permissible pulse repetition frequency.

The above considerations result in a basic arrangement as shown in FIG. 3, in which six sound transducer heads 15 to 20 are sufficient, which have working ranges 15a to 20a that cover the depth between the surface 5 and the boundary 6. Working ranges 15a to 18a correspond to the working ranges 7a to 10a of FIG. 2 but owing to the provision of the pre-entry paths 19b, 20b the two sound transducer heads 19 and 20 are sufficient for examining the zones 19a, 20a near the surface of the object whereas the sound transducer heads 11 to 14 are required for that purpose in the arrangement shown in FIG. 2. In the arrangement shown in FIG. 3, the pre-entry paths can be omitted if an examination of the zones near the surface of the object under improved operating conditions is not required. The arrangements shown in FIGS. 2 and 3 are only illustrative. The conditions will be quantitatively altered if different values are selected for the wavelength, the region to be displayed, and the largest permissible diameter of the sound beam. The quantitative representation has been chosen because it facilitates the understanding of the inventive concept.

FIG. 4 shows that the sound transducer heads 15 to 20 are incorporated in a scanning mechanism, which comprises a wheel 21, which is accommodated in a housing 23 and mounted on a driven shaft 22 for imparting a uniform rotation to the wheel. The housing 23 is sound-permeable at least on the underside and each of the sound transducer heads 15 to 20 is activated as it moves past the sound exit window 25. The peripheral length of the sound exit window will depend on the angular spacing of the sound transducer heads on the wheel. The sound transducer heads 15 to 18 are mounted at the periphery of the wheel. The sound transducer heads 19 and 20 are accommodated in the wheel. The pre-entry paths 19b, 20b are constituted by sound-conducting liquid, which fills passages formed in the wheel body 21. The space between the periphery 21a of the wheel body and the inside surface of the housing 23 is also filled with the sound-conducting liquid. Each passage 19b, 20b has an open end 19c, 20c, respectively, at periphery 21a of wheel body 21 so that the sound conducting liquid in these passages communicates with the sound conducting liquid in the housing. The passage defining the pre-entry path 20b is angled and at the bend is provided with a sound reflector 24. Each of the sound transducer heads 15 to 20 has been shown as a simple generator and owing to the provision of one of the measures described with reference to FIG. 1 is adapted to generate a focused sound beam so that the working ranges 15a to 20a are obtained. Magnetic switches, collector strips revolving in unison with the wheel or slip rings may be used in conjunction with a pulse generator to activate each sound transducer head as it moves past the window 25. Suitable transmitting means are used also to transmit the echo signals from an activated sound transducer head to the amplifying and processing circuitry. The scanning mechanism comprising the wheel may have signal generators associated with it, which during the rotation of the wheel generate address signals for controlling the display. Said address signals indicate which relative angular position of the wheel and of the activated sound transducer heads is associated with the sound pulses which are being emitted and received. These means as well as the other means employed may be basically the same as those known in the art discussed hereinbefore, e.g., disclosed in U.S. Pat. No. 4,102,204. The pulse repetition frequency may be selected in dependence on the maximum depth of penetration which is desired. In the present embodiment the pulse repetition frequency will depend on the transit time of the sound emitted and received by the sound transducer head 15. Because the passage 20b is angled, all axes of the beams exiting from the periphery of the wheel may lie exactly in a plane. Alternatively, the wheel 21 may be thicker and the passages defining the pre-entry paths may be spaced apart in the direction of the axis of the wheel so that the passages cross each other. In that case too, a suitable reflexion may be adopted to ensure that the axis of the sound beam which exits at the open end of the passage will be aligned with the section surface. As will be described hereinafter with reference to FIG. 5, control signals may be directly or indirectly derived from the operation of the scanning mechanism, i.e., from the rotation of the wheel 21, in order to indicate which sound transducer head is activated at a time. These signals may be used to define time slots or to adjust other control devices which ensure that only echo signals corresponding to echoes which have originated in the working range 15a, 16a, 17a, 18a, 19a or 20a of the activated sound transducer head will be forwarded for further processing. At least theoretically the generators of the several sound transducer heads could be equal in size and the sound beams could be focussed in that the annular zones of the generators are excited at different phases so that the different working ranges are obtained. In that case the phase-shifting means controlling the excitation in different phases could be selectively disabled so that the generators will then emit non-focussed beams or focussed beams having the same focal length and each sound head will scan the second surface throughout its depth, provided that at least one sound transducer head has a pre-entry path associated with it. For the normal operation in accordance with the invention, the working ranges of the several sound transducer heads are so selected and their generators are so dimensioned that the sound beams have the same mean diameters and maximum diameters in the several working ranges 15a to 20a.

The equipment represented by the block circuit diagram of FIG. 5 comprises a clock 26, which via a lead 27 controls a control unit 28. The latter comprises a pulse generator for generating pulses for activating the sound transducer heads, receivers for echo signals generated by the sound transducer heads, and signal-processing circuitry, such as a demodulator, a threshold value-setting device, filters, means for depth compensation, and amplifiers. The activating pulses are delivered via lead 29 to the scanning mechanism 30, which as explained in conjunction with FIG. 4 comprises control means for forwarding the signals to that sound transducer head which is just moving past the window 25. Said control means are used also to deliver the echo signals via lead 29 to the unit 28. The signals may be transmitted by a transformer, which has one winding that revolves in unison with the wheel 21 and a second winding, which is stationary. The echo signals which have been received by the unit 28 and have been processed therein are delivered via a lead 31 to an address computer 32, which in dependence on the transit time and the position of the respective sound transducer head computes the coordinates of the locations where the corresponding echoes have originated. For that computation the computer receives the clock pulses from the clock 26 via lead 33 so that the computer can determine the transit time of the echo that has been received as the time which has elapsed since the clock pulse. From the scanning mechanism, electric signals are delivered to the computer 32 via a lead 34 to indicate the instantaneous angular position of the just activated sound transducer head relative to the window 25. The echo signal and the address signal generated by the computer are delivered via a lead 35 to a gate 36. The times when said gate is opened and closed are controlled by the clock pulses delivered via lead 37 and by signals delivered by the scanning mechanism 30 via a lead 38. In this way the gate 36 is controlled in such a manner that only the echo signals derived from echoes that have originated in the working range 15a, 16a, 17a, 18a, 19a, or 20a of the then activated sound transducer head 15, 16, 17, 18, 19 or 20, and the addresses associated with said echo signals, can be delivered to a memory 40 via a lead 39. Echo signals derived from echoes which have not originated in the working range are suppressed as well as the corresponding addresses. The computer 32 also generates and delivers a zero signal so that a zero value is stored at those addresses which are associated with the working range and for which no echo signal has been generated. Because echo signals and address signals associated with locations outside the working range of the activated sound transducer head will be suppressed, the corresponding memory locations will be kept free for echo signals derived from echoes which have originated in the working ranges of other sound transducer heads when these are activated. All memory locations associated with a section surface will receive information during an entire revolution of the wheel. In generating the addresses, the address computer 32 will take also the pre-entry paths 19b, 20b into account. The signals stored in the memory, inclusive of the zero signals stored at memory locations which are associated with the section surface but have not received an echo signal, can be read via a lead 41 by means of a reading unit 42 and can be delivered via a lead 43 to a display unit 44. The reading sequence may be entirely different from the sequence in which the signals have been written into the memory. Reading may be effected at a higher frame frequency than writing so that a flicker-free image can be generated, e.g., by means of a television monitor.

What is claimed is:

1. In ultrasonic examination equipment comprising
   a scanning mechanism including a wheel and drive means for rotating said wheel about its axis,
   a plurality of focussing sound transducer heads carried by said wheel and angularly spaced apart with respect to said axis, each of said sound transducer heads being adapted to be activated to emit sound pulses forming a sound beam, which is projected outwardly of the periphery of said wheel and adapted to enter a section surface of an object to be examined, each of said sound transducer heads when activated being also adapted to receive echo pulses originating in said object in response to said sound pulses, and to derive electric echo signals from said echo pulses, each of said sound transducer heads having a working range which has a near end and a far end spaced apart along said beam, each of said sound beams having in said working range of the sound transducer head emitting said beam a higher resolution than in other length portions of said sound beam,
   activating means for activating each of said sound transducer heads during the movement thereof through a predetermined angular range with respect to said axis, which angular range is not in excess of the angular spacing of adjacent ones of said sound transducer heads with respect to said axis, whereby successive ones of said sound transducer heads are adapted to successively scan said section surface with said sound beams,
   a display unit having a display surface, and signal-processing means arranged to receive said echo signals from said sound transducer heads and in response to said echo signals to cause said display unit to display said echoes on said display surface at locations geometrically coordinated with their origins in said section surface, the improvement residing in that the near ends and far ends, respectively, of angularly adjacent ones of said sound transducer heads are spaced different distances outwardly from the periphery of said wheel, signal-selecting means are provided, which are arranged to deliver to said signal-processing means only those of said echo signals which have been derived from echoes originated in the working range of an activated sound transducer head, and pre-entry path defining means are accommodated in said wheel and define at least one pre-entry path which has a substantial length and is arranged to receive within said periphery said sound beam from one of said sound transducer heads which has a working range having near and far ends which are respectively spaced smaller distances outwardly from said periphery than the near and far ends, respectively, of the working range of another of said sound transducer heads, and to project the last-mentioned sound beam outwardly from said periphery when said sound beam has travelled a substantial distance in said pre-entry path.

2. The improvement set forth in claim 1, wherein said sound transducer heads are arranged so that said sound beams have approximately the same mean diameter and approximately the same maximum diameter in the working ranges of the transmitters from which said sound beams are projected.

3. The improvement set forth in claim 1, wherein said selecting means comprise an electronic gate which is adapted to be opened to deliver echo signals from said transducer heads to said signal-processing means, and gate control means for causing said gate to be open only during the time in which echo signals are derived from echoes which have originated in the working range of the sound transducer head which is activated.

4. The improvement set forth in claim 1, wherein said signal-processing means comprise a buffer memory for storing said echo signals which have been delivered by said signal-selecting means and a reading unit for reading the stored signals from said buffer memory and for delivering the read signals to said display unit.

5. The improvement set forth in claim 1, wherein said one sound transducer head has a sound-emitting surface spaced inwardly from the periphery of said wheel, and said pre-entry path defining means define a pre-entry path extending from said sound-emitting surface to said periphery of said wheel.

6. The improvement set forth in claim 5, wherein said wheel comprises a solid body formed with a passage leading from said sound-emitting surface to the periphery of said wheel, and said pre-entry path-defining means comprise sound-conducting liquid filling said passage.

7. The improvement set forth in claim 5, wherein said pre-entry path is angled and has a bend and said pre-entry path-defining means comprise a reflector for deflecting said sound at said bend.

8. The improvement set forth in claim 6 as applied to ultrasonic equipment wherein said wheel is accommodated in a housing, which is filled with sound-conducting liquid and has a sound exit window which faces the periphery of said wheel and extends in said predetermined angular range, another of said sound transducer heads has a sound-emitting surface which is close to the periphery of said wheel and when said other sound transducer head is in said predetermined angular range is spaced from the outside of said window by a distance of an order of the wavelength of the sound emitted by said sound transducer head, in conjunction with the further improvement residing in that said passage has an open end at the periphery of said wheel so that the sound-conducting liquid in said passage communicates through said open end with said sound-conducting liquid in said housing.

* * * * *